(12) United States Patent
Bui et al.

(10) Patent No.: US 9,072,686 B2
(45) Date of Patent: *Jul. 7, 2015

(54) MASCARA CONTAINING AQUEOUS DISPERSION OF POLYURETHANE AND A HARD WAX

(75) Inventors: Hy Si Bui, Piscataway, NJ (US); Mohamed Kanji, Edison, NJ (US); Chunhua Li, North Plainfield, NJ (US); Bruno Thierry Bavouzet, Gentilly (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/971,323

(22) Filed: Dec. 17, 2010

(65) Prior Publication Data

US 2011/0150807 A1    Jun. 23, 2011

Related U.S. Application Data

(60) Provisional application No. 61/288,003, filed on Dec. 18, 2009.

(51) Int. Cl.
*A61K 8/87* (2006.01)
*A61Q 1/10* (2006.01)
*A61Q 1/00* (2006.01)
*A61K 8/04* (2006.01)
*A61K 8/92* (2006.01)

(52) U.S. Cl.
CPC . *A61K 8/87* (2013.01); *A61K 8/044* (2013.01); *A61K 8/92* (2013.01); *A61K 8/922* (2013.01); *A61K 8/925* (2013.01); *A61K 8/927* (2013.01); *A61Q 1/10* (2013.01)

(58) Field of Classification Search
None
See application file for complete search history.

(56) References Cited

U.S. PATENT DOCUMENTS

| 6,274,131 | B1 * | 8/2001 | Piot et al. | 424/70.7 |
| 6,482,400 | B1 * | 11/2002 | Collin | 424/70.6 |
| 6,884,853 | B1 | 4/2005 | Asaoka et al. | |
| 7,445,770 | B2 * | 11/2008 | Berezkin et al. | 424/59 |
| 2004/0022822 | A1 * | 2/2004 | Poret | 424/401 |
| 2005/0019358 | A1 * | 1/2005 | Pinzon et al. | 424/401 |
| 2006/0078520 | A1 * | 4/2006 | Pays et al. | 424/70.7 |
| 2007/0166257 | A1 * | 7/2007 | Atis | 424/70.7 |
| 2008/0226569 | A1 | 9/2008 | Berezkin et al. | |
| 2009/0022678 | A1 | 1/2009 | Berezkin et al. | |
| 2009/0142289 | A1 | 6/2009 | Arditty et al. | |
| 2011/0097289 | A1 | 4/2011 | Viala et al. | |

FOREIGN PATENT DOCUMENTS

| EP | 1 281 385 A1 | 2/2003 |
| EP | 2 105 126 A1 | 9/2009 |
| JP | 2009-67797 | 4/2009 |
| WO | WO 01/01936 A1 | 1/2001 |
| WO | WO 02/09658 A1 | 2/2002 |
| WO | WO 2009/118106 A1 | 10/2009 |

OTHER PUBLICATIONS

Extended European Search Report issued Jul. 20, 2011, in Patent Application No. 10195802.3.
Office Action issued Aug. 22, 2011, in European Patent Application No. 10195802.3.
Sophie Viala, "Filming agent gives eyes a striking look", Cosmetics Spray Technology Marketing, www.cosma.com, XP 002599685, Apr. 2009, pp. 36-38.
"New Baycusan C product line: Five new ingredients for looking great", BayerMaterialScienceNAFTA.com, XP 002595522, May 21, 2009, pp. 1-3.
U.S. Appl. No. 12/971,255, filed Dec. 17, 2010, Bui.
U.S. Appl. No. 12/971,301, filed Dec. 17, 2010, Bui.
U.S. Appl. No. 13/639,879, filed Oct. 8, 2012, Li, et al.
European Office Action Issued Jan. 23, 2013 in Patent Application No. 10 195 802.3.

* cited by examiner

*Primary Examiner* — Blessing M Fubara
*Assistant Examiner* — Jennifer A Berrios
(74) *Attorney, Agent, or Firm* — Oblon, McClelland, Maier & Neustadt, L.L.P.

(57) ABSTRACT

The invention relates to a composition comprising aqueous polyurethane dispersions and at least one hard wax.

12 Claims, No Drawings

MASCARA CONTAINING AQUEOUS DISPERSION OF POLYURETHANE AND A HARD WAX

CROSS-REFERENCE TO RELATED APPLICATIONS

This application claims the benefit of priority under 35 U.S.C. §119(e) from U.S. Provisional Application Ser. No. 61/288,003, filed Dec. 18, 2009, the entire contents of which is hereby incorporated by reference.

FIELD OF THE INVENTION

The present invention relates to mascara compositions comprising at least one aqueous dispersion of polyurethane and at least one hard wax. The mascara compositions have beneficial cosmetic properties including comfort upon application and improved volumizing eyelashes. Particularly beneficial or improved properties include significantly improved curling and curl retention properties.

DISCUSSION OF THE BACKGROUND

In the past, long-wear, smudge-resistant mascaras were not washable with water. Such mascaras were typically anhydrous. In contrast, mascara compositions which were washable with water were not long-wear or smudge-resistant. Such mascaras typically contained significant amounts of water (for example, oil-in-water emulsions).

Mascaras are in particular prepared on the basis of two types of formulations: aqueous mascaras referred to as cream mascaras, in the form of a dispersion of waxes in water, and anhydrous or low-water-content mascaras, referred to as water-resistant mascaras (referred to as "waterproof"), in the form of dispersions of waxes in organic solvents.

Thickening or filling mascaras are generally known, and these mascaras can impart volume to eyelashes. This effect is generally obtained by depositing a maximum of solid substances onto the eyelashes. Generally speaking, it is through the qualitative and quantitative choice of the solid particles, in particular the waxes, that the application properties sought for such make-up compositions, such as for example their fluidity or consistency, their covering power or their thickening power (also called filling or make-up power), can be adjusted.

In order to adjust the consistency and the cosmetic properties, so-called "soft" waxes, such as beeswax or paraffin wax, are used in combination with so-called "hard" waxes in order to obtain a mascara exhibiting a high solids content and a medium to high consistency, these characteristics being generally necessary for a mascara to be filling.

In addition, the aqueous mascaras mainly contain a surfactant system, for example based on triethanolamine stearate, which makes it possible to obtain a stable dispersion of particles of wax agglomerated in an aqueous phase. This system plays an important part in the obtaining of such a dispersion, in particular at the interface in the interactions between particles of wax.

However, the mascaras described above have the disadvantages of, among other things, being dry, having poor flexibility and/or having poor consistency.

There is thus a need to develop a cosmetic composition, in particular for making up the eyelashes, making it possible to obtain a smooth and homogeneous deposit on the eyelashes, while exhibiting a consistency that is easy to work after application, which has improved volumizing, curling and/or curl retention properties.

SUMMARY OF THE INVENTION

The present invention relates to compositions for keratinous materials (hair, eyelashes, eyebrows) comprising at least one aqueous dispersion of polyurethane and at least one hard wax. Preferably, the composition is a mascara composition.

The present invention relates to compositions for keratinous materials (hair, eyelashes, eyebrows) comprising at least one aqueous dispersion of polyurethane, at least one hard wax, and at least one surfactant having an HLB value greater than or equal to 8. Preferably, the composition is a mascara composition.

The present invention relates to compositions for keratinous materials (hair, eyelashes, eyebrows) comprising at least one aqueous dispersion of polyurethane, at least one hard wax, and at least two surfactants having an HLB value greater than or equal to 8. Preferably, the composition is a mascara composition.

The present invention also relates to methods of treating, caring for and/or making up eyelashes by applying compositions of the present invention to keratinous materials (hair, eyelashes, eyebrows) in an amount sufficient to treat, care for and/or make up the keratinous materials (hair, eyelashes, eyebrows). Preferably, the composition is a mascara composition.

The present invention also relates to methods of improving the volumizing, curling and/or curl retention properties of a composition for keratinous materials (hair, eyelashes, eyebrows), comprising adding to the composition at least one aqueous dispersion of polyurethane and at least one hard wax. Preferably, at least one surfactant having an HLB value greater than or equal to 8 is also added, preferably at least two. Preferably, the composition is a mascara composition.

The present invention also relates to methods of making a composition for keratinous materials (hair, eyelashes, eyebrows) comprising reacting at least one aqueous dispersion of polyurethane and at least one hard wax to form the composition. Preferably, at least one surfactant having an HLB value greater than or equal to 8 is also reacted, preferably at least two.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Water-soluble solvent" is understood to mean a compound which is liquid at ambient temperature and miscible with water (miscibility with water greater than 50% by weight at 25° C. and atmospheric pressure).

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test.

The "kiss" test may involve application of the composition to human keratin material such as hair, eyelashes or eyebrows followed by rubbing a material, for example, a sheet of paper, against the hair, eyelashes or eyebrows after expiration of a certain amount of time following application, such as 2 minutes after application. Similarly, transfer resistance of a composition may be evaluated by the amount of product transferred from a wearer to any other substrate, such as transfer from the hair, eyelashes or eyebrows of an individual to a collar when putting on clothing after the expiration of a certain amount of time following application of the composition to the hair, eyelashes or eyebrows. The amount of composition transferred to the substrate (e.g., collar, or paper) may then be evaluated and compared. For example, a composition may be transfer resistant if a majority of the product is left on the wearer's hair, eyelashes or eyebrows. Further, the amount transferred may be compared with that transferred by other compositions, such as commercially available compositions. In a preferred embodiment of the present invention, little or no composition is transferred to the substrate from the hair, eyelashes or eyebrows.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, eyelashes or eyebrows and evaluating the color of the composition after an extended period of time. For example, the color of a composition may be evaluated immediately following application to hair, eyelashes or eyebrows and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

Aqueous Polyurethane Dispersion

According to the present invention, compositions comprising at least one aqueous dispersion of polyurethane are provided. "Aqueous polyurethane dispersion" as used herein means the aqueous polyurethane dispersions disclosed in U.S. Pat. No. 7,445,770 and/or U.S. Pat. No. 7,452,770, the entire contents of both of which are hereby incorporated by reference.

More specifically, the aqueous polyurethane dispersions of the present invention are preferably the reaction products of:

A) a prepolymer according to the formula:

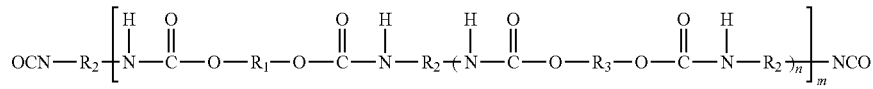

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;

B) at least one chain extender according to the formula: $H_2N-R_4-NH_2$ wherein $R_4$ represents an alkylene or alkylene oxide radical not substituted with ionic or potentially ionic groups; and C) at least one chain extender according to the formula: $H_2N-R_5-NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is chain extended using two classes of chain extenders. First, compounds having the formula: $H_2N—R_4—NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: $H_2N—R_5—NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

The polyurethane according to the invention may also include compounds which are situated in each case at the chain ends and terminate said chains (chain terminators) as described in U.S. Pat. No. 7,445,770 and/or U.S. Pat. No. 7,452,770.

According to preferred embodiments, the aqueous polyurethane dispersion has a viscosity of less than 2000 mPa·s at 23° C., preferably less than 1500, preferably less than 1000, including all ranges and subranges therebetween. Where two or more aqueous polyurethane dispersions are present, it is preferred that all of the aqueous polyurethane dispersions present in the composition have a viscosity of less than 2000 mPa·s at 23° C., preferably less than 1500, preferably less than 1000, including all ranges and subranges therebetween.

According to preferred embodiments, the aqueous polyurethane dispersion has a solids content based on the weigh of the dispersion of from 20% to 60%, preferably from 25% to 55% and preferably from 30% to 50%, including all ranges and subranges therebetween. Where two or more aqueous polyurethane dispersions are present, it is preferred that all of the aqueous polyurethane dispersions present in the composition have a solids content based on the weigh of the dispersion of from 20% to 60%, preferably from 25% to 55% and preferably from 30% to 50%, including all ranges and subranges therebetween.

Suitable aqueous polyurethane dispersions for use in the present invention include, but are not limited to, aqueous polyurethane dispersions sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35).

According to preferred embodiments where two or more aqueous polyurethane dispersions are present, each aqueous polyurethane dispersion is present in the composition of the present invention in a weight ratio ranging from about 5:1 to about 1:5 with respect to each other polyurethane dispersion present in the composition, more preferably from about 3:1 to about 1:3, and more preferably about 1:1, including all ranges and subranges therebetween.

According to preferred embodiments where two or more aqueous polyurethane dispersions are present, at least one of the polyurethanes comprises a hydrophilic portion. For example, commercially available BAYCUSAN® C1000 (polyurethane-34) and BAYCUSAN® C1004 (polyurethane-35) comprise hydrophilic portions. Accordingly, particularly preferred combinations of the present invention include (1) BAYCUSAN® C1000 (polyurethane-34) and/or BAYCUSAN® C1004 (polyurethane-35); and (2) BAYCUSAN® C1001 (polyurethane-34) and/or BAYCUSAN® C1003 (polyurethane-32). A particularly preferred combination is BAYCUSAN® C1004 (polyurethane-35) and BAYCUSAN® C1003 (polyurethane-32).

According to preferred embodiments, the aqueous polyurethane dispersion(s) is (are) present in the composition of the present invention in an amount ranging from about 1 to 35% by weight, more preferably from about 2 to about 30% by weight, more preferably from about 3 to about 20% by weight based on the total weight of the composition, including all ranges and subranges within these ranges.

Hard Wax

According to the present invention, compositions comprising at least one hard wax are provided.

"Wax" means a lipophilic compound, solid at ambient temperature (25° C.), with a reversible solid/liquid change of state, having a melting point greater than or equal to 30° C.

"Hard wax" means a wax exhibiting a hardness greater than 5 MPa, in particular ranging from 5 to 30 MPa, preferably greater than 6 MPa, better still ranging from 6 to 25 MPa, at 20° C. The hardness of the wax can be determined, for example, by measurement of the compression force measured at 20° C. by means of the texturometer sold under the name TA-XT2 by the company RHEO, equipped with a stainless steel cylinder with a diameter of 2 mm moving at the measurement speed of 0.1 mm/s, and penetrating into the wax to a penetration depth of 0.3 mm. A suitable measurement protocol is as follows: the wax is melted at a temperature equal to the melting point of the wax+10° C. The melted wax is poured into a container 25 mm in diameter and 20 mm deep. The wax is recrystallised at ambient temperature (25° C.) for 24 hours so that the surface of the wax is flat and smooth, then the wax is kept for at least 1 hour at 20° C. before performing the measurement of the hardness or the adhesivity. The mobile element of the texturometer is moved at the speed of 0.1 mm/s, then penetrates into the wax to a penetration depth of 0.3 mm. When the mobile element has penetrated into the wax to the depth of 0.3 mm, the mobile element is kept immobile for 1 second (corresponding to the relaxation time) and is then withdrawn at the speed of 0.5 mm/s. The value of the hardness is the maximal compression force measured, divided by the area of the texturometer cylinder in contact with the wax.

The waxes can be hydrocarbon, fluorinated and/or silicone, and be of plant, mineral, animal and/or synthetic origin. Suitable examples of hard wax include, but are not limited to, Carnauba wax, candelilla wax, BIS-PEG-12 DIMETHICONE CANDELILLATE wax such as for example the Siliconyl Candelilla Wax marketed by the company KOSTER KEUNEN, hydrogenated Jojoba wax such as for example that marketed by the company DESERT WHALE, hydrogenated palm oil such as that marketed by the company SIO, rice bran wax, Sumac wax, ceresin waxes, laurel wax, Chinese insect wax, Shellac wax, hydrogenated olive oil such as Waxolive from the company SOLIANCE, waxes obtained by hydrogenation of olive oil esterified with C12 to C18 chain fatty alcohols such as those sold by the company SOPHIM under the brand names Phytowax Olive 12L44, 14L48, 16L55 and 18L57, waxes obtained by hydrogenation of castor oil esterified with cetyl or behenyl alcohol such as for example those which are sold under the names Phytowax Ricin 16 L 64 and Phytowax Ricin 22 L 73 by the company SOPHIM, hydrogenated Cameline wax, Ouricury wax, Montan wax, ozokerite waxes such as for example Wax SP 1020 P marketed by the company Strahl & Pitsch, microcrystalline waxes such as for example that sold under the brand name Microwax HW by the company PARAMELT, triglycerides of lauric, palmitic, cetylic and stearic acids (INCI name: hydrogenated coco glycerides) such as for example that sold under the brand name Softisan 100 by the company SASOL, polymethylene waxes such as for example that sold under the brand name Cirebelle 303 by the company SASOL, polyethylene waxes such as for example those sold under the brand names Performalene 400 polyethylene, Performalene 655 polyethylene and Performalene 500-L polyethylene by the company New Phase Technologies, alcohol-polyethylene waxes such as for example that marketed under the name Performacol 425 Alcohol by the company BARECO, the 95/5 ethylene/acrylic acid copolymer sold under the brand name AC 540 wax by the company Honeywell, hydroxyoctacosanyl hydroxy-stearate such as for example that sold under the brand name Elfacos C 26 by the company AKZO, octacosanyl stearate such as for example that marketed under the name Kester Wax K 82H by the company KOSTER KEUNEN, stearyl stearate such as for example that marketed under the name Liponate SS by the company LIPO CHEMICALS, pentaerythritol distearate such as for example that marketed under the name Cutina PES by the company COGNIS, the mixture of dibehenyl adipate, dioctadecyl adipate and di-eicosanyl adipate (INCI name: C18-C22 dialkyl adipate), the mixture of dilauryl adipate and ditetradecyl adipate (INCI name: C12-C14 dialkyl adipate), the mixture of dioctadecyl sebacate, didocosyl sebacate and dieicosyl sebacate (INCI name: C18-C22 dialkyl sebacate) and the mixture of dioctadecyl octadecanedioate, didocosyl octanedioate and dieicosyl octanedioate (INCI name: C18-C22 dialkyl octanedioate) such as for example those marketed by the company COGNIS, pentaerythrityl tetrastearate such as for example Liponate PS-4 from the company Lipo Chemicals, tetracontanyl stearate such as for example Kester Wax K76H from the company KOSTER KEUNEN, stearyl benzoate such as for example Finsolv 116 from the company FINETEX, behenyl fumarate such as for example Marrix 222 from the company AKZO BERNEL, di-(trimethylol-1,1,1-propane) tetrastearate such as for example that which is offered under the name "HEST 2T-4S" by the company HETERENE, didotriacontanyl distearate such as for example Kester Wax K82D from the company KOSTER KEUNEN, polyethylene glycol montanate with 4 ethylene oxide units (PEG-4) such as for example that which is sold under the brand name Clariant Licowax KST1, hexanediol disalicylate such as for example Betawax RX-13750 marketed by the company CP Hall, dipentaerythritol hexastearate such as for example that which is sold under the brand name Hest 2P-6S by the company HETERENE, ditrimethylolpropane tetrabehenate such as for example that which is sold under the brand name Hest 2T-4B by the company HETERENE, Jojoba esters such as for example that which is sold under the brand name Floraester HIP by the company FLORATECH, mixtures of linear (C20-40) carboxylic acid/saturated hydrocarbons (INCI name: C20-40 acid polyethylene) such as for example Performacid 350 acid from the company NEW PHASE TECHNOLOGIES, synthetic wax of the Fischer-Tropsch type such as that marketed under the name Rosswax 100 by the company ROSS, cetyl alcohol, stearyl alcohol, behenyl alcohol, dioctadecyl carbonate such as for example Cutina KE 3737, saccharose polybehenate such as for example Crodaderm B from the company CRODA, and mixtures thereof, can in particular be cited. Such waxes are also described in U.S. patent application publication no. 2009/0142289, the entire contents of which is hereby incorporated by reference.

Waxes of plant origin such as carnauba wax, candelilla wax, hydrogenated jojoba wax, sumac wax, waxes obtained by hydrogenation of olive oil esterified with C12 to C18 chain fatty alcohols sold by the company SOPHIM in the Phytowax range (12L44, 14L48, 16L55 and 18L57), rice bran wax, cetyl, stearyl and behenyl alcohols, laurel wax and Ouricury wax are preferably used.

The hard wax(es) are preferably present in a quantity of at least 12% by weight, preferably from about 12 to about 30% by weight, preferably from about 14 to about 25% by weight relative to the total weight of the composition, including all ranges and subranges therebetween.

Surfactant Having an HLB Value Greater than or Equal to Eight

According to the present invention, compositions comprising at least one surfactant having an HLB value greater than or equal to 8 are provided. Preferably, the compositions comprise at least two such surfactants, at least three such surfactants, at least four such surfactants, etc. "HLB" means hydrophile-lipophile balance. The HLB value can be determined according to GRIFFIN in J. Soc. Cosm. Chem. 1954 (volume 5), pages 249-256.

These surfactant agents can be selected from non-ionic, anionic, cationic and amphoteric surfactant agents. Reference can be made to the document "Encyclopedia of Chemical Technology, KIRK-OTHMER", volume 22, p. 333-432, 3rd edition, 1979, WILEY, for the definition of the properties and the emulsifying functions of the surfactant agents, in particular p. 347-377 of this reference, for the anionic, amphoteric and non-ionic surfactant agents. Such surfactants are also described in U.S. patent application publication no. 2009/0142289, the entire contents of which is hereby incorporated by reference.

Suitable non-ionic surfactants of HLB greater than or equal to 8, used alone or as a mixture, include:

glycerol ethers, ethoxylated and/or propoxylated, which can contain from 1 to 150 ethylene oxide and/or propylene oxide units;

ethoxylated and/or propoxylated ethers (which can contain from 1 to 150 ethylene oxide and/or propylene oxide units) of fatty alcohols, in particular C8-C24, and preferably C12-C18, such as the ethoxylated ether of stearyl alcohol with 20 ethylene oxide units (CTFA name "Steareth-20") such as the BRIJ 78 marketed by the company UNIQEMA, the ethoxylated ether of cetearyl alcohol with 30 ethylene oxide units (CTFA name "Ceteareth-30") and the ethoxylated ether of the mixture of C12-C15 fatty alcohols containing 7 ethylene oxide units (CTFA name "C12-C15 Pareth-7") such as that marketed under the name NEODOL 25-7® by SHELL CHEMICALS;

fatty acid esters, in particular C8-C24, and preferably C16-C22, and polyethylene glycol (or PEG) (which can contain from 1 to 150 ethylene oxide units), such as the PEG-50 stearate and PEG-40 monostearate marketed under the name MYRJ 52P® by the company UNIQEMA;

fatty acid esters, in particular C8-C24, and preferably C16-C22, and ethoxylated and/or propoxylated ethers of glycerol (which can contain from 1 to 150 ethylene oxide and/or propylene oxide units), such as the polyethoxylated glyceryl monostearate with 200 ethylene oxide units sold under the name Simulsol 220 ™® by the company SEPPIC; polyethoxylated glyceryl stearate with 30 ethylene oxide units such as the product TAGAT S®, sold by the company GOLDSCHMIDT, polyethoxylated glyceryl oleate with 30 ethylene oxide units such as the product TAGAT O® sold by the company GOLDSCHMIDT, polyethoxylated glyceryl cocoate with 30 ethylene oxide units such as the product VARIONIC LI 13® sold by the company SHEREX, polyethoxylated glyceryl isostearate with 30 ethylene oxide units such as the product TAGAT L® sold by the company GOLDSCHMIDT and polyethoxylated glyceryl laurate with 30 ethylene oxide units such as the product TAGAT I® from the company GOLDSCHMIDT;

fatty acid esters, in particular C8-C24, and preferably C16-C22, and ethoxylated and/or propoxylated ethers of sorbitol (which can contain from 1 to 150 ethylene oxide and/or propylene oxide units), such as the polysorbate 60 sold under the name Tween 60® by the company UNIQEMA;

dimethicone copolyol, such as that sold under the name Q2-5220® by the company DOW CORNING;

dimethicone copolyol benzoate such as that sold under the name FINSOLV SLB 101® and 201® by the company FINTEX;

copolymers of propylene oxide and ethylene oxide, also called EO/PO polycondensates, and mixtures thereof.

Suitable anionic surfactants include, but are not limited to, salts of C16-C30 fatty acids, in particular amine salts such as triethanolamine stearate or 2-amino-2-methylpropane-1,3-diol stearate; salts of polyethoxylated fatty acids, in particular amine salts or alkali metal salts, and mixtures thereof; phosphate esters and salts thereof such as "DEA oleth-10 phosphate" (Crodafos N 10N from the company CRODA) or monopotassium monocetyl phosphate (Amphisol K from Givaudan or ARLATONE MAP 160K from the company UNIQEMA); suiphosuccinates such as "Disodium PEG-5 citrate lauryl sulphosuccinate" and "Disodium ricinoleamido MEA sulphosuccinate"; alkyl ether sulphates such as sodium lauryl ether sulphate; isethionates; acylglutamates such as "Disodium hydrogenated tallow glutamate" (AMISOFT HS-21 R®marketed by the company AJINOMOTO) and mixtures thereof.

Suitable cationic surfactants include, but are not limited to, alkylimidazolidiniums such as isostearyl-ethylimidonium etho-sulphate; and ammonium salts such as (C12-C30 alkyl)-tri(C1-C4 alkyl)ammonium halides such as N,N,N-trimethyl-1-docosanaminium chloride (or Behentrimonium chloride).

Suitable amphoteric surfactants include, but are not limited to, N-acyl amino acids such as N-alkyl-aminoacetates and disodium cocoamphodiacetate, and amine oxides such as stearamine oxide, or even silicone surfactants such as the dimethicone copolyol phosphates such as that sold under the name PECOSIL PS 100® by the company PHOENIX CHEMICAL.

According to preferred embodiments, the compositions according to the invention contain the following combination of surfactants: (1) at least one phosphate ester or salt thereof such as "DEA oleth-10 phosphate" or monopotassium monocetyl phosphate; and (2) at least one ethoxylated and/or propoxylated ethers (which can contain from 1 to 150 ethylene oxide and/or propylene oxide units) of fatty alcohols, in particular C8-C24, and preferably C12-C18.

According to preferred embodiments, surfactant(s) having an HLB value of greater than or equal to 8 are present in the composition of the present invention in an amount ranging from about 0.5 to 15% by weight, more preferably from about 2 to about 10% by weight, more preferably from about 3 to about 8% by weight based on the total weight of the composition, including all ranges and subranges within these ranges.

Compositions of the present invention can optionally further comprise any additive usually used in the field(s) under consideration. For example, dispersants such as poly(12-hydroxystearic acid), antioxidants, oils, sunscreens, preserving agents, fragrances, fibers, fillers, neutralizing agents, cosmetic and dermatological active agents such as, for example, emollients, moisturizers, vitamins, essential fatty acids, surfactants having an HLB value of less than 8, silicone elastomers, pasty compounds, viscosity increasing agents such as additional waxes (for example, soft or adhesive waxes) or liposoluble/lipodispersible polymers, film forming agents, colorants, and mixtures thereof can be added. A non-exhaustive listing of such ingredients can be found in U.S. patent application publication nos. 2004/0170586 and 2009/0142289, the entire contents of which are hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

Suitable surfactants having an HLB value less than 8 include, but are not limited to, esters and ethers of sugars such as saccharose stearate, saccharose cocoate, sorbitan stearate and mixtures thereof; esters of fatty acids, in particular C8-C24, and preferably C16-C22, and polyols, in particular glycerol or sorbitol, such as glyceryl stearate, glyceryl laurate, polyglyceryl-2 stearate, sorbitan tristearate, and glyceryl ricinoleate; ethoxylated and/or propoxylated ethers such as the ethoxylated ether of stearyl alcohol with 2 ethylene oxide units (CTFA name "Steareth-2"); and a mixture of cyclomethicone/dimethicone copolyol such as that sold under the name Q2-3225C® by the company DOW CORNING.

Suitable oils include volatile and/or non-volatile oils. Such oils can be any acceptable oil including but not limited to silicone oils and/or hydrocarbon oils.

According to certain embodiments, the oil carrier comprises one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |

TABLE 1-continued

| Compound | Flash Point (° C.) | Viscosity (cSt) |
| --- | --- | --- |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other embodiments, the oil carrier comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to other embodiments of the present invention, the oil carrier comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments of the present invention, the compositions can further comprise a desired agent. The desired agent can be, for example, any colorant (pigment, dye, etc.), any pharmaceutically or cosmetically active agent, or any film forming agent known in the art. For example, a cosmetic makeup composition or a paint composition comprising colorant can provide colorant and/or film forming agent to a substrate (skin, lips, wall, frame, etc.) during use to provide the substrate with the desired film and/or color. Similarly, a pharmaceutical or cosmetic composition comprising a pharmaceutically active agent can provide such active agent to the patient or consumer upon use.

Acceptable colorants include pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, Acceptable film forming agents and/or rheological agents are known in the art and include, but are not limited to, those disclosed in U.S. patent application publication no. 2004/0170586, the entire contents of which is hereby incorporated by reference.

Non-limiting representative examples of acceptable film forming/rheolgocial agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film forming/rheological agents also include water soluble polymers such as, for example, high molecular weight crosslinked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof.

Suitable fibers include, but are not limited to, fibers which enable improvement of the lengthening effect. "Fiber" should be understood to mean an object of length L and diameter D such that L is much greater than D, D being the diameter of the circle in which the cross-section of the fibre is inscribed. In particular, the L/D ratio (or form factor) is selected in the band ranging from 3.5 to 2500, in particular from 5 to 500, and more particularly from 5 to 150. The fibers utilisable in the composition of the invention can be fibers of synthetic or natural origin, mineral or organic. They can be short or long, unitary or structured, for example, braided, hollow or full. They can be of any shape and in particular of circular or polygonal cross-section (square, hexagonal or octagonal) depending on the specific application envisaged. In particular, their ends are blunted and/or polished to avoid injury. They can be rigid or non-rigid fibers. They can be of synthetic or natural origin, mineral or organic. They can be surface treated or not, coated or not, and colored or not.

According to preferred embodiments of the present invention, the compositions comprise substantial amounts of water. Preferably, compositions of the present invention comprise from about 5% to about 80% water, more preferably from about 15% to about 60% water, and more preferably from about 20% to about 50% water by weight with respect to the total weight of the composition, including all ranges and subranges therebetween.

In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

Another preferred embodiment of the present invention is a composition which contains so little TEA-stearate that the presence of TEA-stearate does not affect the cosmetic properties of the composition. Preferably, the compositions are substantially free of TEA-stearate (i.e., contain less than about 0.5% TEA-stearate), essentially free of TEA-stearate (i.e., contain less than about 0.25% TEA-stearate) or free of TEA-stearate (i.e., contain no TEA-stearate).

According to other preferred embodiments, methods of treating, caring for and/or enhancing the appearance of keratinous material by applying compositions of the present invention to the keratinous material in an amount sufficient to treat, care for and/or enhance the appearance of the keratinous material are provided. In accordance with these preceding preferred embodiments, the compositions of the present invention are applied topically to the desired area of the keratin material in an amount sufficient to treat, care for and/or enhance the appearance of the keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved waterproof characteristics, improved feel upon application (for example, texture, reduced drag or tackiness), increased anti-smudging properties, increased volume properties, increased curling properties, increased curl retention properties and/or increased long wear properties are provided.

According to other embodiments of the present invention, methods of improving the anti-smudging, volumizing, waterproof, transfer-resistance, curling, curling retention and/or long wear properties of a composition, comprising adding at least one hard wax and at least two aqueous polyurethane dispersions are provided.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example

Mascara Composition

Step 1: Preparation of the Base Mascara Composition

| Phase | Chemical Name | Trade Name | % wt/wt |
|---|---|---|---|
| B | Steareth-2 | | 2.10 |
| B | Steareth-20 | | 4.45 |
| B | Cetyl Alcohol | | 2 |
| B | Rice Bran Wax | | 12.00 |
| B | Candelilla Wax | | 4.00 |
| B | Carnuaba Wax | | 8.00 |
| B | Ethylparaben | | 0.20 |
| B | Iron Oxides | Sunpuro Black Iron Oxide C33-7001 | 8.00 |
| A | DI Water | DI Water | 50.00 |
| A | Disodium EDTA | Disodium EDTA | 0.10 |
| A | Potassium Cetyl Phosphate | Amphisol K | 1.60 |
| A | Methylparaben | Methylparaben | 0.25 |
| A | Pentylene Glycol | Hydrolite-5 | 2.00 |
| A | Hydroxyethylcellulose | | 0.80 |
| A | 50% Sodium Hydroxide | | 0.50 |
| A | *Acacia* Gum | | 3.40 |
| A | Simethicone | Mirasil SM | 0.10 |
| A | Phenoxyethanol | | 0.50 |
| | | Total % | 100.00 |

Procedure:
1. In a suitable size metal container, phase B ingredients (except iron oxides) were added and heated to 90° C. (until all solids have melted and become uniform).
2. Iron oxides were added, and the batch was homogenized at 900 RPM for at least 1 hour.
3. In a side tank with water bath, the gums were pre-wet in water, then all the materials in phase A were added and the contents were heated 90° C.
4. When both tanks were at temperature, phase A (water phase) was slowly added to B (oil phase) while homogenizing at 500 RPM.
5. After mixture was uniform, using a planetarian blade, it was homogenized at 50 RPM and mixed mechanically with stirring rod.
6. Phenoxyethanol was added at 55° C.

Step Two: Blend Polyurethane Dispersions into Mascara Base

| Phase | Component | Example 1 | Example 2 | Example 3 | Example 4 |
|---|---|---|---|---|---|
| A | Mascara Base from step 1 | 82 | 76 | 85 | 82 |
| A | Polyurethane-34 Baycusan C1000 (solid ~40%) | 18 | | | |
| A | Polyurethane-34 Baycusan C1001 (solid 32%) | | 24 | | |
| A | Polyurethane-32 Baycusan C1003 (solid ~50%) | | | 15 | |
| A | Polyurethane-35 Baycusan C1004 (Solid ~41%) | | | | 18 |
| | Total | 100 | 100 | 100 | 100 |
| | Curling effect | Good | no | excellent | Excellent |

Procedure:
1. Heat the Mascara Base from step 1 to 55° C.
2. Blend Polyurethane dispersions into the Mascara base at low shear 50 RPM until the batch becomes uniform.
3. In all the cases, the solid concentration of polyurethane is around 7% solid.

Curl and Curl Retention Study

The compositions were directly applied onto fake eyelashes by applying the compositions in the same direction for 30 strokes. Then, force was applied to the lashes in the same direction to "curl" or bend the lashes. Then, the amount of bend or curl (as determined by angle to normal) was measured after 30 minutes and again after 3 hours.

The composition containing C1000 had an initial angle of 12° after 30 min and 10° after 3 hours. This composition displayed good curl and curl retention properties.

The composition containing C1003 had an initial angle of 19° after 30 min and 16° after 3 hours. This composition displayed good curl and curl retention properties.

The composition containing C1004 had an initial angle of 21° after 30 min and 22° after 3 hours. This composition displayed good curl and curl retention properties.

What is claimed is:

1. A composition comprising at least one aqueous polyurethane dispersion having a solid content of from 40% to 50% based on the weight of the dispersion and the at least one aqueous polyurethane dispersion is selected from the group consisting of polyurethane-32 and polyurethane-35;
   at least 12% by weight with respect to the total weight of the composition of at least one wax exhibiting a hardness greater than 5 MPa at 20° C.;
   at least one surfactant having an HLB value greater than or equal to 8, and
   at least one surfactant having an HLB value less than 8.
2. The composition of claim 1, in the form of a mascara.
3. The composition of claim 1, wherein the composition is an emulsion.
4. The composition of claim 1, further comprising a fatty alcohol.
5. The composition of claim 1, wherein the aqueous polyurethane dispersion is present in an amount from 1% to 35% of the total weight of the composition.
6. The composition of claim 2, wherein the aqueous polyurethane dispersion is present in an amount from 1% to 35% of the total weight of the composition.
7. The composition of claim 1, wherein at least two aqueous polyurethane dispersions are present.
8. The composition of claim 7, wherein each aqueous polyurethane dispersion is present in the composition in a weight ratio ranging from 3:1 to 1:3 with respect to each other aqueous polyurethane dispersion present in the composition.

9. A method of retaining curling in eyelashes comprising applying the composition of claim 1 to eyelashes.

10. A method of making up eyelashes comprising applying the composition of claim 2 to eyelashes.

11. The composition of claim 1, wherein the at least one wax is present in an amount from 12% to 30% by weight of the total weight of the composition.

12. The composition of claim 1, wherein the at least one wax is present in an amount from 14% to 25% by weight of the total weight of the composition.

* * * * *